US010195562B2

(12) United States Patent
Belliveau

(10) Patent No.: US 10,195,562 B2
(45) Date of Patent: Feb. 5, 2019

(54) APPARATUSES, METHODS, AND SYSTEMS FOR REMOVAL OF TARGET COMPOUNDS FROM GASES

(71) Applicant: EMPIRE TECHNOLOGY DEVELOPMENT LLC, Wilmington, DE (US)

(72) Inventor: Daniel Alderic Belliveau, Bellevue, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 142 days.

(21) Appl. No.: 15/303,195

(22) PCT Filed: Apr. 9, 2014

(86) PCT No.: PCT/US2014/033423
§ 371 (c)(1),
(2) Date: Oct. 10, 2016

(87) PCT Pub. No.: WO2015/156787
PCT Pub. Date: Oct. 15, 2015

(65) Prior Publication Data
US 2017/0028344 A1    Feb. 2, 2017

(51) Int. Cl.
*B01D 53/14* (2006.01)
*B01D 53/72* (2006.01)
(Continued)

(52) U.S. Cl.
CPC ..... *B01D 53/1456* (2013.01); *B01D 53/1406* (2013.01); *B01D 53/1412* (2013.01);
(Continued)

(58) Field of Classification Search
CPC ............ B01D 53/1406; B01D 53/1412; B01D 53/1456; B01D 53/1487; B01D 53/18;
(Continued)

(56) References Cited

U.S. PATENT DOCUMENTS 3,928,005 A    12/1975    Laslo
5,104,665 A     4/1992    Fleet et al.
(Continued)

FOREIGN PATENT DOCUMENTS

| CA | 2881218 A1 | 2/2014 |
| DE | 202010017655 U1 | 5/2012 |
| EP | 0818231 A1 | 1/1998 |

OTHER PUBLICATIONS

International Search Report and Written Opinion for International Application No. PCT/US2014/033423, dated Aug. 22, 2014, pp. 16.
(Continued)

*Primary Examiner* — Frank M Lawrence, Jr.
(74) *Attorney, Agent, or Firm* — IP Spring

(57) ABSTRACT

Systems and methods for reducing a target molecule in a fluid are described. A fluid, such as a gas, may be contacted with a fluid capable of binding with the target molecules and removing the target molecules from the fluid. For example, emissions from a production process may be contacted with water to remove volatile organic compound (VOCs), thereby reducing the VOCs in the emissions. The fluid with bound target molecules may form a target fluid that may be discharged from the system or may be reused until the concentration of the target molecules in the target fluid reaches a threshold concentration. An illustrative production process is the fermentation of wine, which produces an off-gas that includes VOCs, such as ethanol. The systems
(Continued)

and methods for reducing a target molecule may significantly reduce or even eliminate the amount of ethanol in the fermentation off-gas.

21 Claims, 3 Drawing Sheets

(51) Int. Cl.
    *B01D 53/78*     (2006.01)
    *B01D 53/79*     (2006.01)
    *B01D 53/18*     (2006.01)
    *C12M 1/00*     (2006.01)

(52) U.S. Cl.
    CPC ......... *B01D 53/1487* (2013.01); *B01D 53/18* (2013.01); *B01D 53/72* (2013.01); *B01D 53/78* (2013.01); *B01D 53/79* (2013.01); *C12M 47/18* (2013.01); *B01D 2252/103* (2013.01); *B01D 2257/708* (2013.01); *B01D 2258/0275* (2013.01)

(58) Field of Classification Search
    CPC ........ B01D 53/72; B01D 53/78; B01D 53/79; B01D 2252/103; B01D 2257/708; B01D 2258/0275; C12M 47/18
    USPC ....... 95/8, 13, 187, 199, 224, 235–237, 240; 96/244; 423/220–229, 235, 243.01, 423/245.1, 246
    See application file for complete search history.

(56) References Cited

U.S. PATENT DOCUMENTS

| | | | |
|---|---|---|---|
| 5,156,819 A | 10/1992 | Ross | |
| 5,531,801 A * | 7/1996 | Sewell | B01D 47/06 96/240 |
| 5,565,180 A | 10/1996 | Spink | |
| 5,690,899 A * | 11/1997 | Makkinejad | B01D 53/507 423/243.01 |
| 5,756,047 A * | 5/1998 | West | A61L 2/18 422/124 |
| 6,068,686 A * | 5/2000 | Sorensen | B01D 47/14 261/111 |
| 6,409,802 B1 | 6/2002 | Kyotani | |
| 6,475,266 B2 | 11/2002 | Hayashi et al. | |
| 6,955,794 B2 | 10/2005 | Houston, Jr. et al. | |
| 7,932,065 B2 * | 4/2011 | Medoff | C08H 8/00 435/165 |
| 8,398,758 B2 * | 3/2013 | Nagayasu | B01D 53/1418 96/243 |
| 8,961,915 B1 * | 2/2015 | Zhao | B01D 53/58 423/237 |
| 2009/0095162 A1 * | 4/2009 | Hargis | B01D 53/263 96/245 |
| 2011/0120308 A1 | 5/2011 | Dube et al. | |
| 2011/0165663 A1 | 7/2011 | Davis | |
| 2011/0277633 A1 | 11/2011 | Sonnek et al. | |
| 2012/0067219 A1 | 3/2012 | Ogawa et al. | |
| 2012/0214215 A1 | 8/2012 | Sibik | |
| 2015/0209725 A1 * | 7/2015 | Czarnecki | B01D 53/30 423/243.01 |

OTHER PUBLICATIONS

Schick, Spray Technology Reference Guide: Understanding Drop Size, Spray Systems Co. (Sep. 22, 2008), pp. 1-36.
Extended European Search Report for European Application No. 14889132.8 dated Sep. 22, 2017, pp. 12.

* cited by examiner

APPARATUSES, METHODS, AND SYSTEMS FOR REMOVAL OF TARGET COMPOUNDS FROM GASES

CROSS-REFERENCE TO RELATED APPLICATION

This application is a U.S. national stage filing under 35 U.S.C. § 371 of International Application No. PCT/US2014/033423 filed on Apr. 9, 2014 entitled "APPARATUSES, METHODS, AND SYSTEMS FOR REMOVAL OF TARGET COMPOUNDS FROM GASES," which is incorporated herein by reference in its entirety.

BACKGROUND

The regulation of emissions has become increasingly broader and stricter. More compounds are now covered and the amount of many compounds that can be released into the environment has decreased over time. This trend of rising national and state constraint on emissions has put increased pressure on numerous industries to control the release of compounds. For example, the United States Environmental Protection Agency (EPA) has set the legal limit of volatile organic compound (VOC) emissions to 10 tons per year (about 55 pounds per day) before control or capture technology is required. With growing unfavorable sentiment towards any potential negative effects on population health and the environment due to emissions of VOCs, it is likely that the emission of VOCs will be restricted further in the future. Such regulation would have an impact on producers that generate VOCs, such as the wine and beer industry that release VOCs as part of the fermentation process.

In general, manufacturers and producers recognize the need to limit the release of pollutants and ultimately desire to comply with national and state guidelines. However, conventional technology capable of controlling or capturing the release of pollutants is generally inefficient and expensive to operate. In addition, the resources required to retrofit existing facilities to meet emissions guidelines are largely cost-prohibitive. As such, manufacturers and producers are challenged with complying with emissions regulations while maintaining the profitability of their production processes. Accordingly, it would be beneficial to have an efficient and cost-effective system for reducing target pollutants from emissions and, in particular, a system that be used as an economical option to retrofit existing production facilities to control emissions.

SUMMARY

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In an embodiment, an apparatus configured to remove target molecules from a gas may include at least one fluid discharge component configured to discharge fluid particles capable of binding with the target molecules. At least one reaction vessel may be configured to receive the gas. The at least one fluid discharge component may be positioned within the at least one reaction vessel such that the fluid particles contact the gas to form a target fluid comprising the target molecules bound to the fluid particles, thereby reducing a concentration of the target molecules in the gas.

In an embodiment, a method of removing target molecules from a gas may include receiving the gas within at least one reaction vessel. A concentration of the target molecules in the gas may be reduced by discharging fluid particles capable of binding with the target molecules within the at least one reaction vessel such that the fluid particles contact the gas to form a target fluid comprising the target molecules bound to the fluid particles.

In an embodiment, a method of making an apparatus configured to remove target molecules from a gas may include providing at least one reaction vessel configured to receive the gas and providing at least one fluid discharge component configured to discharge fluid particles capable of binding with the target molecules. The at least one fluid discharge component may be arranged within the at least one reaction vessel such that the fluid particles discharged from the at least one fluid discharge component contact the gas to form a target fluid comprising the target molecules bound to the fluid particles, thereby reducing a concentration of the target molecules in the gas.

In an embodiment, a system configured to discharge a gas generated through a process may include a gas source configured to provide a stream of the gas in which the gas may include target molecules. At least one reaction vessel may be in fluid communication with the gas source and configured to receive the stream of the gas. At least one fluid source may be configured to store a fluid capable of binding with the target molecules. At least one fluid discharge component may be positioned within the at least one reaction vessel. The at least one fluid discharge component may be configured to discharge the fluid from the at least one fluid source as fluid particles within the at least one reaction vessel to form a target fluid comprising the target molecules bound to the fluid particles, thereby reducing a concentration of the target molecules in the gas. The system may also include at least one collection container in fluid communication with the at least one reaction vessel that is configured to receive the target fluid. At least one outlet may be in fluid communication with the at least one reaction vessel and may be configured to discharge the gas having a reduced concentration of the target molecules from the system.

DETAILED DESCRIPTION

The terminology used in the description is for the purpose of describing the particular versions or embodiments only, and is not intended to limit the scope.

The described technology generally relates to apparatuses, systems, and methods for reducing the concentration of target compounds, materials, or molecules (the "target molecules") from emissions. The emissions may include a fluid, such as a gas. For example, the fluid may include a gas generated through a manufacturing or production process (the "production process"). The target molecules may generally include pollutants or other compounds that are to be removed from the emissions before the emissions are captured, flow into another phase of the production process, and/or are released into the environment. The emissions and, therefore, the target molecules arranged therein may be contacted with a fluid and/or fluid particles capable of binding with the target molecules and removing them from the emissions (for example, through dielectric interaction between the fluid and the target molecules). In this manner, the fluid particles may act as a filter, removing the target molecules from the emissions as the emissions pass through the fluid particles, thereby reducing a concentration of the target molecules within the emissions. The fluid with the target molecules may form a target fluid, which may be discharged to waste, recycled, converted to compound products, or the like. The emissions with the reduced concentration of the target molecules may be released into the environment, captured, and/or flow to another phase of the production process.

Use of the described technology can result in a reduction or elimination of target molecules in emissions generated through a production process relative to operation of the same or similar production process without the described methods and apparatuses. The concentration of the target molecules in the emissions can generally be reduced by any amount. For example, the concentration of the target molecules can be reduced by at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, and in an ideal situation, about 100% reduction (complete elimination of the target molecules from the emissions).

Figure 1:
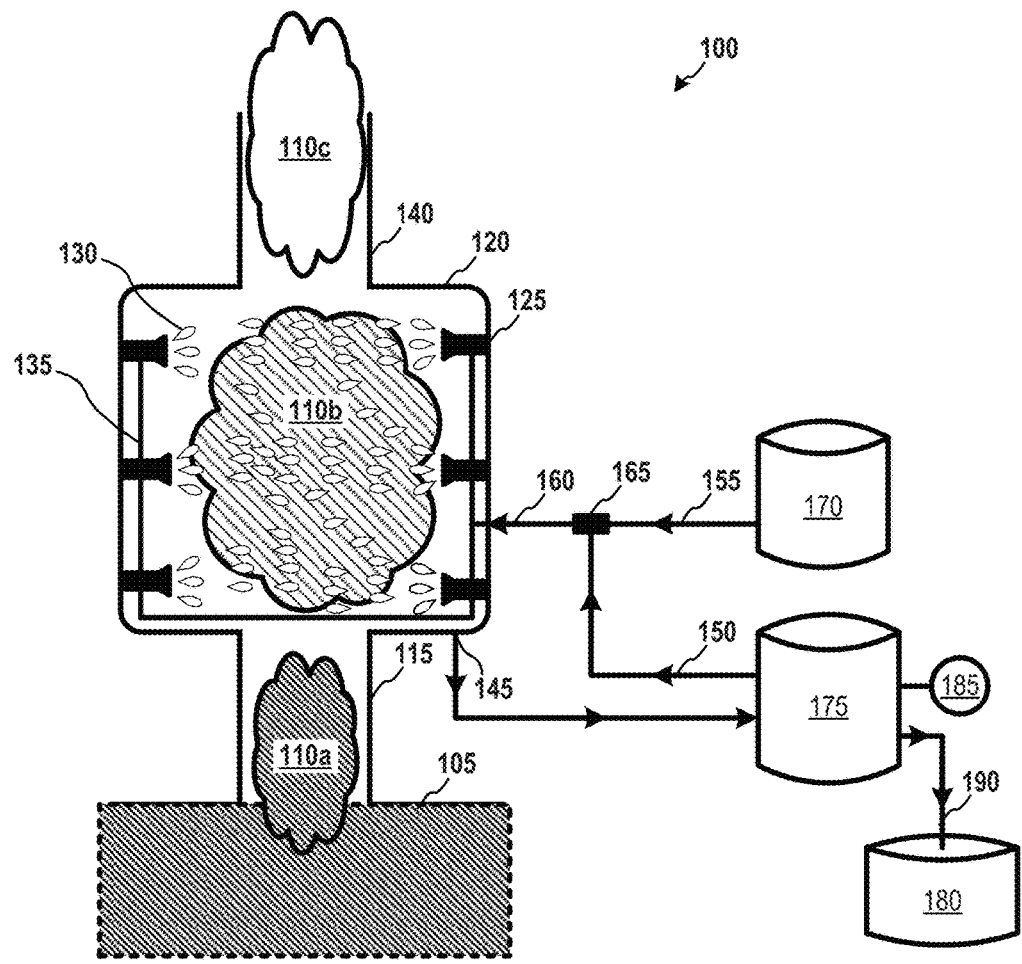
FIG. 1 depicts an illustrative reactor system according to some embodiments.

FIG. 1 depicts an illustrative target molecule reduction system according to some embodiments. As shown in FIG. 1, a target molecule reduction system (the "system") 100 may include a gas source 105 that may provide a gas 110a to the system. Gases 110a-110c depicted in FIG. 1 are the same emission gas, differing in their concentration of the target molecule as the gas flows through the system 100 as described in more detail below. In some embodiments, the gas 110a may be generated through a manufacturing process, a production process, a power production process, or any other type of industrial process. The gas 110a may include a target molecule (not shown, see FIG. 2) at a first concentration. In some embodiments, the gas 110a may include one target molecule. In some embodiments, the gas 110a may include multiple target molecules. In some embodiments, the target molecule may include a pollutant, such as a pollutant regulated by the United States Environmental Protection Agency (EPA), a state environmental protection agency, the European Environmental Agency, or any other similar regulatory entity. In some embodiments, the target molecule may be a compound that is being harvested from the gas 110a. In some embodiments, the target molecule may include a compound produced in a first part of a production process that is required to be removed before the gas 110a is subjected to a second part of the production process. Example target molecules may include organic acids, ethers, alcohols, amines, nitriles, ketones, and aldehydes. In general, the target molecule may include any compound selected to be removed from or have its concentration reduced in the gas 110a. Non-limiting examples of target molecules may include volatile organic compounds (VOCs), methanol, ethanol, propanol (for example, 2-propanol), butanol, pentanol, hexanol, formaldehyde, tetrahydrofuran, furan, d-Limonene, toluene, acetone, acetic acid, acetonitrile, ether, glycol, glycerin, methyl tertiary-butyl ether (MTBE), dioxane, dimethylformamide (DMF), pyridine, methyl chloride, carbon dioxide, carbon monoxide, nitrogen dioxide, dichloromethane, benzene, and sulfur dioxide.

The gas 110a may include a gas having a first concentration of the target molecules. The concentration of the gas 110a, or any other gas described herein, may depend on various factors including, without limitation duration of the fermentation cycle, sugar content, temperature, volume, pressure, yeast variation, and other process and product variables. In some embodiments, the first concentration may be the highest concentration of the target molecules within the system 100 as the concentration of the target molecules may be greatest at the gas source 105. The gas 110a may flow into a reaction vessel 120 through an inlet 115. In some embodiments, the inlet 115 may be an emissions exhaust for a production process, and the system 100 may be configured to clean (or "scrub") the gas 110a before it is released into the environment or into another process. The reaction vessel 120 may include any type of vessel, tank, container, or other receptacle capable of receiving the gas 110a. The reaction vessel 120 may be formed from various materials configured to handle the gas 110a and any other fluids used within the system 100, including, without limitation, metal, metal alloys, ceramic, high density poly-ethylene (HDPE), low density poly-ethylene (LDPE), gel coated fiberglass, PVC material, ridgid or flexible rubberized cloth and extruded or welded plastics or plex-glass, and combinations thereof alone or in combination with one or more protective coatings. The reaction vessel 120 may have a size and shape configured to receive the gas 110a from the gas source 105. In some embodiments, the reaction vessel 120 may have a substantially cylindrical shape, a rectangular shape, a circular shape, or any combination thereof. In some embodiments, the reaction vessel 120 may have a height of about 0.3 meters to about 10 meters and a width of about 0.3 meters to about 10 meters. In some embodiments, the reaction vessel 120 may be configured to receive the gas 110a at generally any rate, such as a rate of about 5 liters per minute, about 10 liters per minute, about 50 liters per minute, about 100 liters per minute, about 500 liters per minute, about 1000 liters per minute, about 2000 liters per minute, about 3000 liters per minute, and any range between any of these values (including endpoints). Although only one reaction vessel 120 is depicted in FIG. 1, embodiments are not so limited, as the system 100 may include any number of reaction vessels arranged in various configurations, such as multiple reaction vessels arranged in parallel and/or in series.

The reaction vessel 120 may include fluid discharge components 125. The fluid discharge components 125 may be configured to discharge fluid particles 130 within the reaction vessel 120. Although there are multiple fluid discharge components 125 and fluid particles 130 depicted in FIG. 1, only one fluid discharge component and fluid particle are labeled to simplify the figure. In some embodiments, the fluid discharge components 125 may include a spray nozzle, such as a conical spray nozzle (i.e., a spray nozzle that creates a conical or substantially conical spray pattern). The system 100 may include multiple fluid discharge components 125 arranged in various configurations. For instance, the system 100 may include about 2 to about 1000 fluid discharge components 125, about 5 to about 1000 fluid discharge components, about 10 to about 500 fluid discharge components, about 50 to about 500 fluid discharge components, about 100 to about 500 fluid discharge components, about 10 to about 100 fluid discharge components, about 50 to about 100 fluid discharge components, about 2 fluid discharge components, about 5 fluid discharge components, about 10 fluid discharge components, about 50 fluid discharge components, about 100 fluid discharge components, about 500 fluid discharge components, about 1000 fluid discharge components, and any value or range between any two of these values (including endpoints). The fluid discharge components 125 may be arranged in various configurations, such as a linear configuration or in one or more arrays. The fluid discharge components 125 may be configured to discharge the fluid particles 130 in various directions, including an upward direction (for example, in the same direction that the gas 110b travels through the reaction vessel 120), downward, perpendicular to the direction of gas flow, at an angle, or a combination thereof.

The fluid discharge components 125 may be configured to discharge the fluid particles 130 such that at least a portion of the fluid discharge particles contacts the gas 110b within the reaction vessel 120. In some embodiments, the fluid discharge components 125 may be in operable connection with a fluid discharge control component (not shown) configured to control the operation of the fluid discharge components. For example, the fluid discharge control component may be configured to control the type of discharged fluid, a total amount of discharged fluid, a flow rate, a discharge duration, a discharge pressure, a direction of flow, which fluid discharge components 125 are active, or the like. The fluid discharge components 125 may be configured to discharge the fluid particles 130 for a particular time period, including about 30 seconds, about 1 minute, about 2 minutes, about 5 minutes, about 10 minutes, about 30 minutes, about 1 hour, about 2 hours, about 5 hours, about 10 hours, about 12 hours, about 1 day, about 4 days, about 7 days, about 10 days, about 17 days, or any value or range between any of these two values (including endpoints). In some embodiments, the fluid discharge components 125 may be configured to discharge the fluid particles 130 responsive to the production of the gas 110a by the production process 105 and/or the detection of the gas 110a, 110b within the reaction vessel 120. In some embodiments, the fluid discharge components 125 may be configured to discharge the fluid particles 130 in a ratio with respect to the volume of gas 110a, 110b, for instance, the fluid discharge components may be configured to discharge the fluid to achieve a gas-to-fluid particles ratio of about 1:100, about 1:50, about 1:25, about 1:10, about 1:5, about 1:2, or any value or range between any two of these values (including endpoints). For a system 100 having $CO_2$ off-gas carrying ethanol target molecules, the ratio of $CO_2$ off-gas to ethanol being carried out of the system may be about 25:1, 50:1, 100:1, 200:1, 500:1, 1000:1, and any value or range between any two of these values (including endpoints).

The fluid particles 130 may be formed from any type of fluid and/or mixture of fluids capable of binding with the target molecules within the gas 110b. For instance, the fluid may include, without limitation, water, hydrogen peroxide, alcohols (for example, any diol, triol, glycol, glycerin), organic acids, organic acid water solutions, ionic liquids, solvents, amines (for example, methanol amine and other aqueous amines), alkyl carbonates, acetaldehyde, any combinations thereof, hydrophilic solvents, and any ionized versions thereof. In some embodiments, water may be used as a carrier of water-soluble materials capable of binding with the target molecules.

In some embodiments, the fluid discharge components 125 may discharge the fluid particles 130 as a spray or mist. In some embodiments, the fluid particles 130 may be formed as fluid droplets. The droplets may have various sizes. In some embodiments, smaller droplets may be used to increase the contact surface area between the fluid particles and the gas 110a. In some embodiments, the reaction speed of the fluid particles binding with the target molecules may be proportional to the contact surface area. In some embodiments, the droplets may an average diameter of about 1 µm, about 2 µm, about 5 µm, about 10 µm, about 20 µm, about 25 µm, about 50 µm, about 60 µm, about 80 µm, about 100 µm, about 500 µm, about 1000 µm, and about 1500 µm. In some embodiments, the fluid droplets may have an average diameter of about 1 µm to about 2 µm, about 1 µm to about 5 µm, about 1 µm to about 10 µm, about 10 µm to about 20 µm, about 10 µm to about 50 µm, about 20 µm to about 60 µm, about 25 µm to about 80 µm, about 1 µm to about 100 µm, about 10 µm to about 100 µm, about 50 to about 100 µm, about 25 µm to about 100 µm, about 1 µm to about 200 µm, about 50 µm to about 200 µm, about 1 µm to about 500 µm, about 50 µm to about 500 µm, about 100 µm to about 500 µm, about 1 µm to about 1000 µm, about 100 µm to about 1000 µm, about 500 µm to about 1000 µm, about 1 µm to about 1500 µm, about 500 µm to about 1500 µm, about 1000 µm to about 1500 µm and any range between any of these values (including endpoints).

The fluid discharge component may include any type of spray nozzle for generation of spray or mist having desirable particle sizes. In one embodiment, the spray nozzle may have one outlet (single outlet nozzle) or more outlets (a compound nozzle). In one embodiment, the spray nozzle may be a single-fluid nozzle, a multiple-fluid nozzle, a rotary atomizer, or an ultrasound atomizer. The single-fluid nozzle may include a plain orifice nozzle, a shaped-orifice nozzle, a surface-impingement single-fluid nozzle, a pressure-swirl single-fluid spray nozzle, a solid-cone single-fluid nozzle, or a compound nozzle. In some embodiments, a multiple-fluid nozzle may include an internal-mix nozzle or an external-mix nozzle.

A fluid source 170 may store at least a portion of the fluid used for the fluid particles 130. The fluid source 170 may provide the fluid within the system 100 through a fluid source path 155. The fluid source path 155 may be in fluid communication with a fluid inlet 160 configured to allow the fluid to enter a fluid supply circuit 135 that supplies the fluid to the fluid discharge components 125.

In some embodiments, the system 100 may include one or more fluid sources 170 configured to provide a particular fluid, such as water or a solvent. In some embodiments, the system 100 may include multiple fluid sources 170 configured to provide different fluids. In some embodiments having multiple fluid sources 170, the different fluids may be discharged into the reaction vessel 120 simultaneously, each through a separate fluid discharge component 125, for instance, to bind with different target molecules or for particular conditions (for example, target molecule concentrations, temperatures, pressures, or the like). In some embodiments having multiple fluid sources 170, the different fluids may be combined to form a mixture that is discharged from the fluid discharge components 125. In some embodiments, multiple types of target molecules may be removed from the gas 110b at the same time, for example, by using fluid particles 130 capable of binding to the multiple types of target molecules and/or using multiple types of fluid particles, with each of the multiple types of fluid particles capable of binding with at least one of the multiple types of target molecules.

The fluid particles 130 may contact the gas 110b and may bind with the target molecules within the gas 110b. Fluid particles 130 bound with the target molecules may form a target fluid that includes the fluid particles with the target molecules arranged therein. In some embodiments, the target fluid may be formed as a mixture, a solution, a colloid, a suspension, a dispersion, or any combination thereof. In some embodiments, the fluid particles 130 may react with the target molecules to form a target fluid that is a separate compound. The target fluid may be discharged from the reaction vessel 120 through an outlet 145 and into a target fluid storage container 175.

In some embodiments, the fluid particles 130 may include at least a portion of the target fluid stored in the target fluid storage container 175. In this manner, the target fluid may be reused or recycled within the system 100. A concentration monitor 185 may be configured to measure the concentration of the target molecules in the target fluid, for instance, stored in the target fluid storage tank (or collection container) 175. The concentration monitor 185 may include any type of device capable of measuring the concentration of a target molecule in the target fluid known to those having ordinary skill in the art. In some embodiments, a target fluid having a concentration of the target molecule above a threshold amount may be discharged from the target fluid storage container 175, for instance, through an outlet 190 and into a waste system 180 (or, alternatively, into a processing system). In some embodiments, a target fluid having a concentration of the target molecule (the "recyclable target fluid") below the threshold amount may be used as at least a portion of the fluid particles 130. In some embodiments, the threshold concentration of the target molecule may be about 1%, about 2%, about 5%, about 10%, about 12%, about 15%, about 20%, about 30%, about 40%, about 50%, about 1% to about 12%, about 2% to about 10%, about 5% to about 10%, about 8% to about 12%, about 10% to about 50%, about 20% to about 30%, about 30% to about 50%, or any value or range between any of these values (including endpoints).

The target fluid storage container 175 may be in fluid communication with the fluid inlet 160 such that the recyclable target fluid may be fed into the fluid supply circuit 135. In some embodiments, a fluid controller 165 may be configured to control the fluid entering the fluid inlet 160. The fluid controller 165 may include one or more valves and/or control devices configured to control the entry of fluid from the fluid source 170 and the recyclable target fluid from the target fluid storage container 175. For example, the fluid controller 165 may prevent the entry of fluid from the fluid source 170 if there is an adequate supply of the recyclable target fluid. In another example, the fluid controller 165 may ensure a certain mixture of the fluid from the fluid source 170 and the recyclable target fluid, such as a 50%/50% by or 90%/10% volume mixture of both fluids.

As the fluid particles 130 contact the gas 110b, the fluid particles bind with the target molecules within the gas, reducing the concentration of the target molecules within the gas. For instance, and without limitation, the gas 110c released from the reaction vessel 120 through the gas outlet 140 may have a concentration of the target molecules that is about 70% to about 90% less than the concentration of the target molecules in the gas 110a.

As described above, use of the system 100 can result in a reduction or elimination of target molecules in emissions. The concentration of the target molecules in the gas 110a can generally be reduced by any amount. For example, the concentration of the target molecules can be reduced by at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, and in an ideal situation, about 100% reduction (complete elimination of the target molecules from the emissions).

In some embodiments, the system 100 may be configured to capture a certain percentage (capture percentage) at a certain efficiency (efficiency percentage), such as an about 90% capture percentage at an about 90% efficiency percentage for an about 81% total capture efficiency. For VOCs, the daily allowance of emissions may be measured in pounds of VOCs discharged per day and emission capture efficiencies being measured in % capture. In some embodiments, the system 100 may operate with a % capture of about 70% to about 95% (Best Available Control Technology (BACT) requires a % capture of about 80%).

In some embodiments, the gas 110c may be released into the environment as a cleaner emission gas having a lower concentration of the target molecule as would be released in a production process that did not use the system 100. For instance, the gas 110a may have a concentration of about 0.1% to about 15% of the target molecule while the gas 110c released from the reaction vessel may have a concentration of about 0.05%, about 0.1%, about 0.5%, about 1%, about 2%, about 3%, about 4%, about 5%, and any range between any of these values (including endpoints). In some embodiments, the gas 110c may be passed through one or more additional reaction vessels 120 (not shown, see FIG. 3) for additional cleaning or "scrubbing." In some embodiments, the gas 110c may be used in additional production processing steps.

Figure 2:
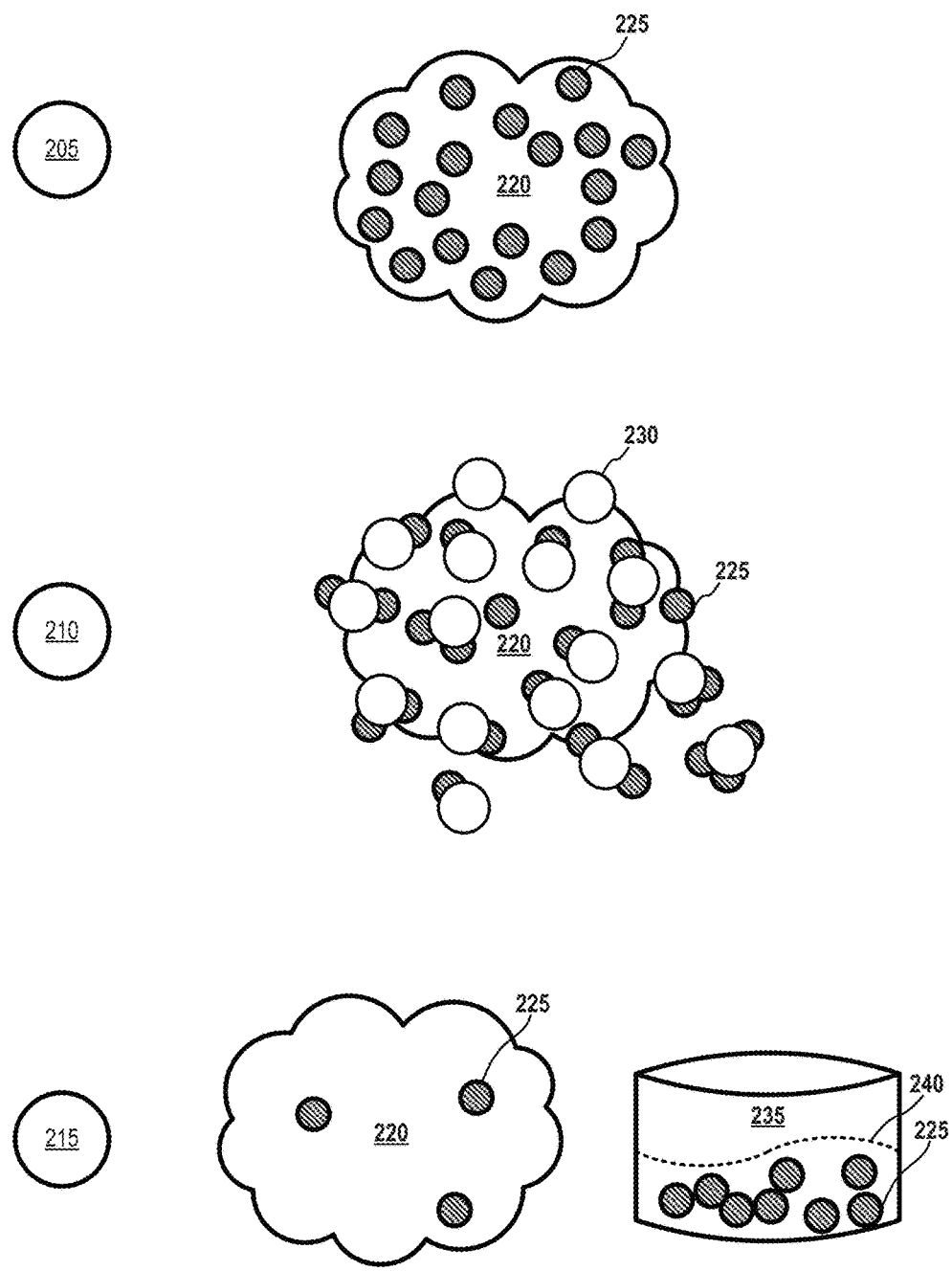
FIG. 2 depicts an illustrative target molecule removal process using fluid particles according to some embodiments.

FIG. 2 depicts an illustrative target molecule removal process using fluid particles according to some embodiments. As shown in FIG. 2, at step 205, a volume of gas 220 may include a first concentration of target molecules 225. In some embodiments, the target molecules 225 may include multiple types of compounds, such as ethanol and carbon dioxide. In step 210, fluid particles 230 may be contacted with the volume of gas 220a. The fluid particles 230 may bind with the target molecules 225 within the volume of gas 220. In some embodiments, the fluid particles 230 may include particles formed from multiple types of fluids. For example, the fluid particles 230 may include water to bind with ethanol target molecules 225 and an aqueous amine to bind with carbon dioxide. In step 215, a target fluid 240 has been formed that includes the target molecules 225 arranged within the fluid used to form the fluid particles. The target fluid 240 may be stored in a container 235. As shown in step 215, the concentration of the target molecules 225 in the volume of gas 220 may be significantly reduced as compared with the concentration of the target molecules in the volume of gas depicted in step 205. For example, and without limitation, the concentration of the target molecules 225 in the volume of gas 220 may be reduced by about 70% to about 95%.

Figure 3:
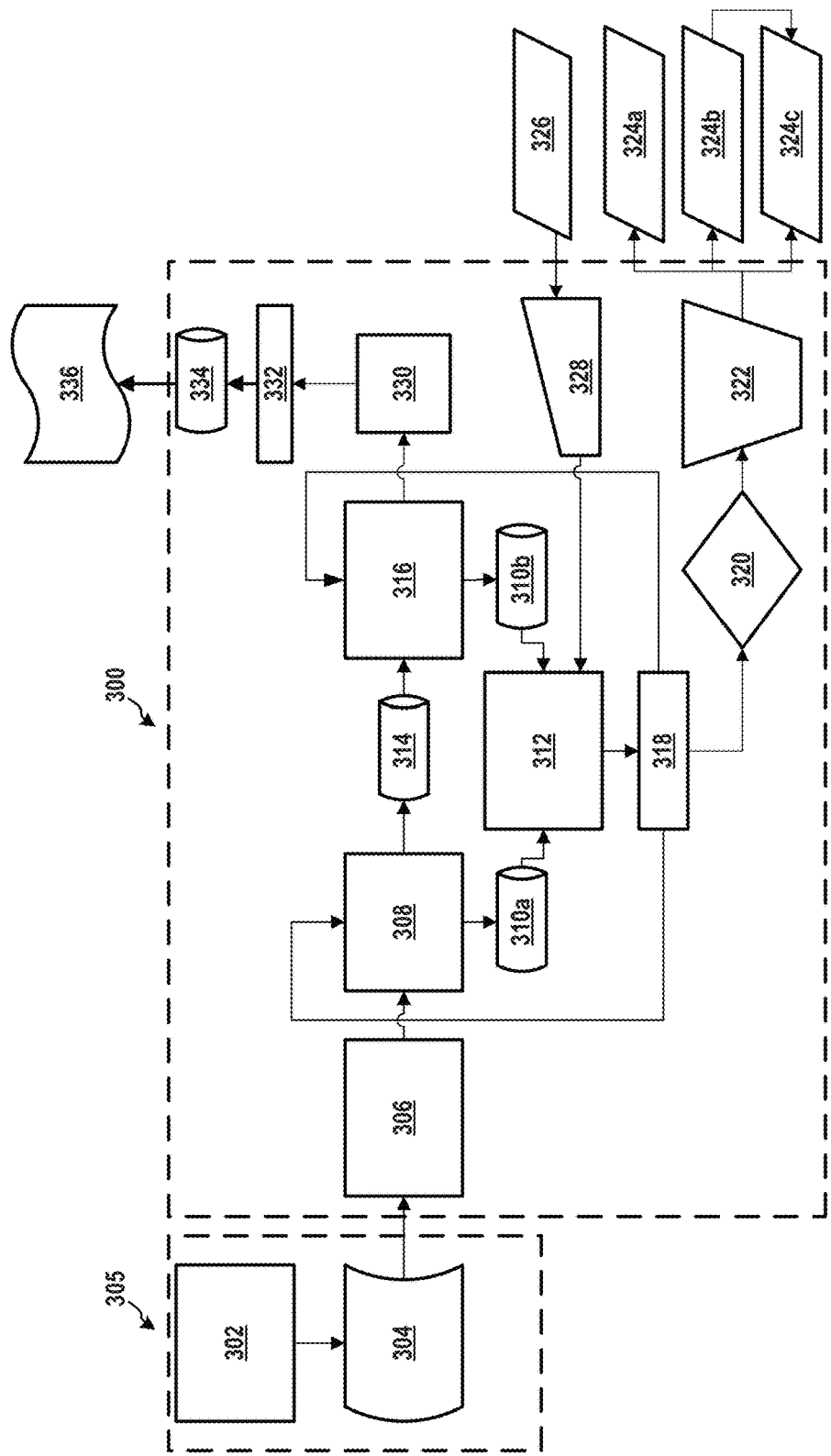
FIG. 3 depicts a flow diagram for an illustrative method of reducing a target molecule from an emitted fluid according to an embodiment.

FIG. 3 depicts an illustrative target molecule reduction system according to some embodiments. As shown in FIG. 3, a target molecule reduction system 300 (the "system")

may be in fluid communication with a production process 305 to capture target molecules within a fluid or gas emitted through the production process (the "emitted fluid"). The production process 305 may include any process that generates an emitted fluid containing target molecules that may be captured by the system 300, including, without limitation, a fermentation process, a manufacturing process, and a power production process.

The production process 305 may include an emitted fluid generation process 302 that may generate an emitted fluid source 304 that is fed into the system 300 through an emitted fluid in-feed flow control 306. The emitted fluid may flow into a first reaction vessel 308 having fluid discharge elements configured to discharge fluid particles capable of binding the target molecules within the emitted fluid. The fluid particles may be derived from fluid stored within a slurry tank 312. At least a portion of the fluid in the slurry tank 312 may come from a fluid source 326, such as an external fluid source, configured to supply the fluid to a fluid recharge component 328 configured to recharge the slurry tank 312. For instance, for water fluid particles, the fluid source 326 may be a municipal water supply.

The fluid particles that bind with the target molecules may form a target fluid 310a that flows into the slurry tank 312. The emitted fluid 314 that passes through the first reaction vessel 308 may flow into a second reaction vessel 316 for a second stage of cleaning or "scrubbing." The second reaction vessel 316 may also include discharge elements configured to discharge fluid particles capable of binding the target molecules within the emitted fluid. The fluid particles that bind with the target molecules within the second reaction vessel 316 may form a target fluid 310b that flows into a slurry tank 312.

The system 300 may include a target fluid recycling component 318 configured manage the reuse of the target fluid, for instance, until the concentration of the target molecules in the target fluid reaches a threshold concentration. The concentration of the target molecules in the target fluid may be monitored using a slurry concentration monitor 320. If the concentration of target molecules in the target fluid is less than a threshold concentration, the target fluid in the slurry tank 312 may be used as at least a portion of the fluid particles in the first reaction vessel 308 and/or the second reaction vessel 316. If the concentration of target molecules in the target fluid is greater than a threshold concentration, the target fluid in the slurry tank 312 may be diluted to a concentration of target molecules that is less than the threshold concentration by supplying fluid from the fluid recharge component 328 and/or the target fluid may be discharged 322 into one or more discharge destinations, including, without limitation, consumer by-products 324a, a sanitation reuse system 324b, or a managed waste system 324c.

The emitted fluid that passes through the second reaction vessel 316 may flow to an emitted fluid discharge flow control 330. The emitted fluid may be subjected to additional processing such as filtration 332 and pollutant (for example, non-target molecules) capture devices 334, such as $CO_2$. The cleaned emitted fluid may be released 336 from the system 300 with a greatly reduced concentration or even the complete elimination of the target molecules from the emitted fluid.

EXAMPLES

Example 1: Reduction of Ethanol from Wine Fermentation Off-Gas

A wine production facility includes a malolactic fermentation tank configured to produce about 200,000 liters of wine that produces an off-gas with volatile organic compounds (VOCs), such as ethanol, over the course of the fermentation cycle. The malolactic fermentation process converts glucose ($C_6H_{12}O_6$) to ethanol ($C_2H_5OH$), and stoichiometrically produces carbon dioxide ($CO_2$): $C_6H_{12}O_6 \rightarrow 2C_2H_5OH + 2CO_2$. The $CO_2$ carries VOCs mainly in the form of ethanol. The untreated off-gas will include about 265 liters, or about 210 kilograms, of ethanol to be carried out of the fermentation tank via $CO_2$ off-gassing per day. The U.S. Environmental Protection Agency (EPA) limits the VOC release for the wine production facility to 25 kilograms per day.

The off-gas from the malolactic fermentation tank flows into a conduit that is in fluid communication with a cylindrical reaction vessel formed from steel and having a ceramic material coating the inner surface thereof. The reaction vessel is formed from two reaction columns, each about 10 meters tall and having a diameter of about 3 meters. The reaction vessel is arranged in a vertical orientation and receives the off-gas through an inlet positioned at a bottom portion thereof. The off-gas flows from the bottom portion, up along the longitudinal axis of the reaction vessel, and out through an outlet in a top portion of the reaction vessel.

Conical spray nozzles are arranged along the inner surface of the reaction vessel, with 10 conical spray nozzles arranged on a first side and 10 arranged on a second side that is opposite the first side. A water tank is connected to and is configured to supply water to the conical spray nozzles. A spray control module is operably connected to the spray nozzles and is configured to open the conical spray nozzles and to control the spray pressure of fluid from the spray nozzles. The ability to mount a flow meter that is operably connected to the spray control module and is positioned at the lower portion of the reaction vessel. The flow meter is configured to detect the flow of off-gas through the inlet.

The ability to use a spray control module to open the conical spray nozzles responsive to receiving a signal from the flow meter that off-gas is flowing through the inlet. The conical spray nozzles will discharge water droplets having an average diameter of about 100 μm that contact the off-gas flowing through the reaction vessel. Ethanol has a high solubility in water because ethanol and water are each polar molecules that form hydrogen bonds. As such, the water droplets will contact the target ethanol molecules, and will form a bond therewith. The water droplets, including water droplets bound to ethanol molecules, will be collected in a target fluid tank and will be used for consumer by-products that use ethanol as a constituent. The water droplets will remove about 90% of the ethanol from the off-gas before the off-gas is discharged into the environment through the reaction vessel outlet. Accordingly, only about 21 kilograms per day of VOCs are discharged into the environment from the wine production facility. In addition, the wine production facility generates about a 4 kilogram-per-day surplus of allowed VOC emissions, which it is able to sell on the regional emissions credit market.

Example 2: Reduction of Ethanol from Beer Fermenter Off-Gas

At an ale beer fermenter in a beer production facility, cooled wort is transferred into a 9,085 liter fermentation tank to which yeast has already been added. The wort is maintained at a constant temperature of 20° C. for about two weeks. When the wort is first added to the yeast, the specific gravity of the mixture is measured. The specific gravity of the mixture is subsequently measured during the fermentation process to determine how much alcohol is in the beer and to know when to stop the fermentation.

The fermenter is sealed off from the air except for a long narrow vent pipe, which allows off-gas containing carbon dioxide and VOC such as ethanol to escape from the fermenter. The vent pipe is connected with an inlet of a reaction vessel formed from steel. The reaction vessel is measured about 1 meter long about 1 meter wide and about 2 meters tall.

The off-gas from the fermenter flows into a conduit that is in fluid communication with the reaction vessel. The reaction vessel is arranged in a vertical orientation and receives the off-gas through an inlet positioned at a bottom portion thereof. The off-gas flows from the bottom portion, up along the longitudinal axis of the reaction vessel, and out through an outlet in a top portion of the reaction vessel.

Spray nozzles are arranged along the inner surface of the reaction vessel, with 8 spray nozzles arranged on a first side and 8 arranged on a second side that is opposite the first side. A water tank is connected to and is configured to supply water to the spray nozzles. A spray control module is operably connected to the spray nozzles and is configured to open the spray nozzles and to control the spray pressure of fluid from the spray nozzles. A flow meter that is operably connected to the spray control module is positioned at the lower portion of the reaction vessel. The flow meter is configured to detect the flow of off-gas through the inlet.

The spray nozzles discharge water droplets having an average diameter of about 200 µm that contact the off-gas flowing through the reaction vessel. Ethanol in the off-gas is dissolved and binds with water droplets to form ethanol water solution droplets. The ethanol water solution droplets are collected in a target fluid tank. The water droplets remove about 83% of the ethanol from the off-gas before the off-gas is discharged into the environment through the reaction vessel outlet.

Example 3: Reduction of Ethanol from Biomass Fermenter Exhaust

In an ethanol production process, raw biomass is subjected to acidic pretreatment and saccharification to provide a liquid solution high in monomeric sugars. The sugar solution is placed into a fermenter in which the monomeric sugars are fermented into ethanol using microorganisms such as yeasts. The concentrations of sugar and ethanol are monitored over the course of fermentation in order to ensure that the fermentation is proceeding optimally. The off-gas is piped off the fermentation tank through a venting pipe. The vent pipe is connected with an inlet of a reaction vessel formed from steel. The reaction vessel is formed from two columns that are each about 1 meter wide about 1 meter long about 2 meters tall.

The off-gas from the fermenter flows into a conduit that is in fluid communication with the reaction vessel. The reaction vessel is arranged in a vertical orientation and receives the off-gas through the inlet positioned at a bottom portion thereof. The off-gas flows from the bottom portion, up along the longitudinal axis of the reaction vessel, and out through an outlet in a top portion of the reaction vessel.

Spray nozzles are arranged along the inner surface of the reaction vessel, with 10 spray nozzles arranged on a first side and 10 arranged on a second side that is opposite the first side. A water tank is connected to and is configured to supply water to the spray nozzles. A spray control module is operably connected to the spray nozzles and is configured to open the spray nozzles and to control the spray pressure of fluid from the spray nozzles. The spray nozzles discharge water droplets having an average diameter of about 80 µm that contact the off-gas flowing through the reaction vessel. Ethanol in the off-gas dissolves and binds with water droplets to form ethanol water solution droplets. The ethanol water solution droplets are collected in a target fluid tank. The water droplets remove about 93% of the ethanol from the off-gas before the off-gas is discharged into the environment through the reaction vessel outlet.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to"). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example), the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, or the like. As a non-limiting example, each range discussed herein can be readily broken down into a lower third, a middle third, and an upper third. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. An apparatus configured to remove ethanol from a gas, the apparatus comprising:
    at least one fluid discharge component configured to discharge fluid particles capable of forming a hydrogen bond with ethanol, wherein the at least one fluid discharge component comprises a plurality of conical spray nozzles, and wherein the plurality of conical spray nozzles create a conical or substantially conical spray pattern;
    at least one reaction vessel configured to receive the gas, the at least one fluid discharge component being positioned within the at least one reaction vessel such that the fluid particles form a hydrogen bond with ethanol in the gas to form a target fluid, thereby reducing a concentration of ethanol in the gas;
    at least one collection container in fluid communication with the at least one reaction vessel and configured to receive the target fluid; and
    a concentration monitor configured to monitor the concentration of ethanol in the target fluid disposed within the at least one collection container.

2. The apparatus of claim 1, wherein the fluid discharge component is in fluid communication with the at least one collection container, and wherein at least a portion of the fluid particles discharged by the fluid discharge component comprises target fluid received from the at least one collection container.

3. The apparatus of claim 1, further comprising a target fluid discharge component configured to discharge the target fluid responsive to the concentration of ethanol reaching a threshold concentration.

4. The apparatus of claim 1, further comprising at least one outlet in fluid communication with the at least one reaction vessel and configured to discharge the gas having a reduced concentration of ethanol from the apparatus.

5. The apparatus of claim 1, wherein the fluid particles comprise one or more of water droplets and hydrophilic solvent droplets.

6. The apparatus of claim 1, wherein the fluid particles comprise fluid droplets having an average diameter of about 10 μm to about 100 μm.

7. The apparatus of claim 1, wherein the concentration of ethanol in the gas is reduced by about 100%.

8. The apparatus of claim 1, wherein the concentration of ethanol in the gas is reduced by about 50% to about 100%.

9. The apparatus of claim 1, wherein the at least one reaction vessel comprises a first reaction vessel in fluid communication with a second reaction vessel, the first reaction vessel being configured to transfer the gas to the second reaction vessel, and wherein the concentration of ethanol in the gas is reduced to a first reduction level within the first reaction vessel and to a second reduction level within the second reaction vessel.

10. The apparatus of claim 9, wherein the first reduction level is at least about a 50% reduction of ethanol in the gas and the second reduction level is at least about a 90% reduction of ethanol in the gas.

11. The apparatus of claim 1, wherein the gas is a by-product of a fermentation process.

12. The apparatus of claim 1, wherein the at least one reaction vessel comprises a dielectric reaction vessel, and wherein a dielectric interaction occurs between fluid particles and ethanol in the dielectric reaction vessel.

13. A method of removing ethanol from a gas, the method comprising:
   receiving the gas within at least one reaction vessel;
   reducing a concentration of ethanol in the gas by discharging fluid particles in a conical or substantially conical pattern, wherein the fluid particles are capable of forming a hydrogen bond with ethanol within the at least one reaction vessel such that the fluid particles contact the gas to form a target fluid comprising ethanol bound to the fluid particles;
   collecting the target fluid within at least one collection container in fluid communication with the at least one reaction vessel; and
   monitoring ethanol concentration in the target fluid disposed within the at least one collection container.

14. The method of claim 13, wherein reducing the concentration of ethanol comprises discharging fluid particles including water droplets.

15. The method of claim 13, wherein reducing the concentration of ethanol comprises discharging fluid droplets having an average diameter of about 10 µm to about 100 µm.

16. The method of claim 13, wherein receiving the gas comprises receiving the gas in the at least one reaction vessel as a continuous gas stream.

17. The method of claim 13, wherein reducing the concentration of ethanol comprises reducing the concentration by about 50% to about 100%.

18. The method of claim 13, further comprising discharging the target fluid responsive to ethanol concentration reaching a threshold concentration.

19. The method of claim 13, further comprising:
   configuring the at least one reaction vessel as a first reaction vessel in fluid communication with a second reaction vessel, the first reaction vessel being configured to transfer the gas to the second reaction vessel;
   reducing the concentration of ethanol in the gas to a first reduction level within the first reaction vessel; and
   reducing the concentration of ethanol in the gas to a second reduction level within the second reaction vessel.

20. The method of claim 19, wherein reducing the concentration of ethanol in the gas to a first reduction level comprises reducing to a level of at least about a 50% reduction of ethanol in the gas, and reducing the concentration of the ethanol in the gas to a second reduction level comprises reducing to a level of at least about a 90% reduction of ethanol in the gas.

21. The method of claim 13, wherein receiving the gas comprises receiving by-product of a fermentation process in an alcohol production process.

* * * * *